United States Patent [19]

Pomato et al.

[11] Patent Number: 5,338,832
[45] Date of Patent: Aug. 16, 1994

[54] ANTIGEN RECOGNIZED BY MCA 16-88

[75] Inventors: Nicholas Pomato, Frederick, Md.; Ebo S. Bos, De Veiesstratt, Netherlands; Martin V. Haspel, Silver Spring, Md.; Michael G. Hanna, Jr., Frederick, Md.; Michael L. Berman, Potomac, Md.

[73] Assignee: Akzo N.V., Velperweg, Netherlands

[21] Appl. No.: 929,842

[22] Filed: Aug. 13, 1992

Related U.S. Application Data

[63] Continuation of Ser. No. 343,475, Feb. 28, 1989, abandoned, which is a continuation-in-part of Ser. No. 69,478, Jul. 2, 1987, abandoned.

[51] Int. Cl.$^5$ .................. C07K 13/00; C07K 5/00; C07K 15/28
[52] U.S. Cl. .................. 530/350; 530/388.85; 530/388.8; 530/387.5; 530/327
[58] Field of Search ............ 530/350, 387.5, 388.85, 530/327, 388.8

[56] References Cited

U.S. PATENT DOCUMENTS

| | | | |
|---|---|---|---|
| 4,727,021 | 2/1988 | Cote et al. | 530/350 |
| 4,828,991 | 5/1989 | Hanna et al. | 435/70.21 |

OTHER PUBLICATIONS

Starling et al. Cancer Research 48 7273-7278 Dec. 15, 1988.
Holmann et al., "Monoclonal antibody–defined Circulating Human Tumor Associated Antigen with Epitope", biochemical and Biophysical Research Communications, vol. 128, No. 1, issued Apr. 16, 1985, p. 34.
Raychaudhuri et al., "Tumor-Specific Idiotype Vaccines. I. Generation and Characterization of Internal Image Tumor Antigens", The Journal of Immunology, vol. 137, No. 5, issued Sep. 1, 1986,; 1743–1749.
Marx, "Making Antibodies Without the Antigens", Science, vol. 228, issued Apr. 12, 1985, pp. 162–165.
Magnani, J. L. et al., Cancer Res. (1983) 43:5489–5492.
Meissner, P. S. et al., Proc. Natl. Acad. Sci. USA (1987) 84:000–0000.
Cancer Research, vol. 12, issued Dec., 1984, USA, Schmidt et al., "Characterization of Monoclonal Antibodies to Novikoff Hepatoma Cytokeratin Antigen p39", pp. 5867–5879.
Franklin et al., "A Monoclonal Antibody Recognizes an Epitope Common to an Avian Specific Nuclear Antigen and to Cytokeratins", Journal of Cellular Biochemistry, vol. 24, issued 1984, pp. 1–14.
Koprwoska et al., "Common Antigenic Sites on Exfoliated Cells Derived from Cervical Carcinoma and in Tumor Cells of Nonuterine Origin as Demonstrated by Monoclonal Antibodies in Immunoperoxidase Assay", Cancer Research, vol. 45, No. 11, issued Nov., 1985, pp. 5964–5968.
Silverberg, E., CA (1983) 33:9–25.
Goligher, J. C., Surgery of the Anus, Rectum and Colon, 4th Ed., London: Baillere Tindall (1980) 47–471.
Hoover, H. C., Jr. et al., Cancer (1985) 55:1236–1243.
Gold, P. and Freedman, S. O., Journal Exp. Med. (1965) 122:467–481.

(List continued on next page.)

*Primary Examiner*—Paula K. Hutzell
*Assistant Examiner*—Lila Feisee
*Attorney, Agent, or Firm*—William M. Blackstone; Mary E. Gormley

[57] ABSTRACT

The present invention comprises the epitope recognized by the human monoclonal antibody 16-18, the human tumor antigen containing this epitope, which we have identified, isolated and characterized, and anti-idiotypic antibodies to human MCA 16-88, which comprise the same epitope. The invention also relates to the use of antibodies to the antigen containing this epitope for diagnosis and monitoring of treatment of cancer and to the use of this antigen in the preparation of vaccines to elicit an immune response similar to that obtained against tumor cells containing this epitope.

4 Claims, 6 Drawing Sheets

OTHER PUBLICATIONS

Yeoman, L. C. et al., Juman Colon Tumor Antigens. In: H. Busch and L. C. Yeoman (eds). vol. 19, 2310271, N.Y. Academic Press, Inc. (1982).

Artigas, C. et al., Cancer Research (1986) 45:1874–1881.

Blaszczyk, M. et al., Cancer Research (1984) 44:245–253.

Ross, A. H., et al., Biochem. Biophys. Res. Comm. (1986) 135:297–303.

Haspel, M. V. et al., Cancer Res. (1985) 45:3951–3961.

Bowser-Finn, R. A., et al.

Shinnick, T. M. et al., "Synthetic Peptide Immunogens as Vaccine", In: Annual review of Microbiologic, vol. 37, Annual Review, Inc. (1983).

Norrby, E. et al. J. Virol. (1986) 58(2):536–541.

Touitou, I. et al., Biochemic (1985) 67:1257–1266.

Probhakas, B. S. et al., "Monoclonal Antibody Techniques Applied to Viruses".: Methods in Virology, vol. 7, N.Y. Academic Press, Inc. (1984).

Laemmli, U. K., Nature (London) 1970, 227:680–685.

Lambin, P. and Fine, J. M., Anal. Biochem. 1979, 98:160–168.

Towbin, H. et al., Proc. Natl. Acad. Sci. USA (1979) 76:4350–4354.

Cote, R. J., et al., Proc. Natl. Acad. Sci. USA (1986) 83:2959–2963.

Romano, V. et al., Diff (1986) 30:244–253.

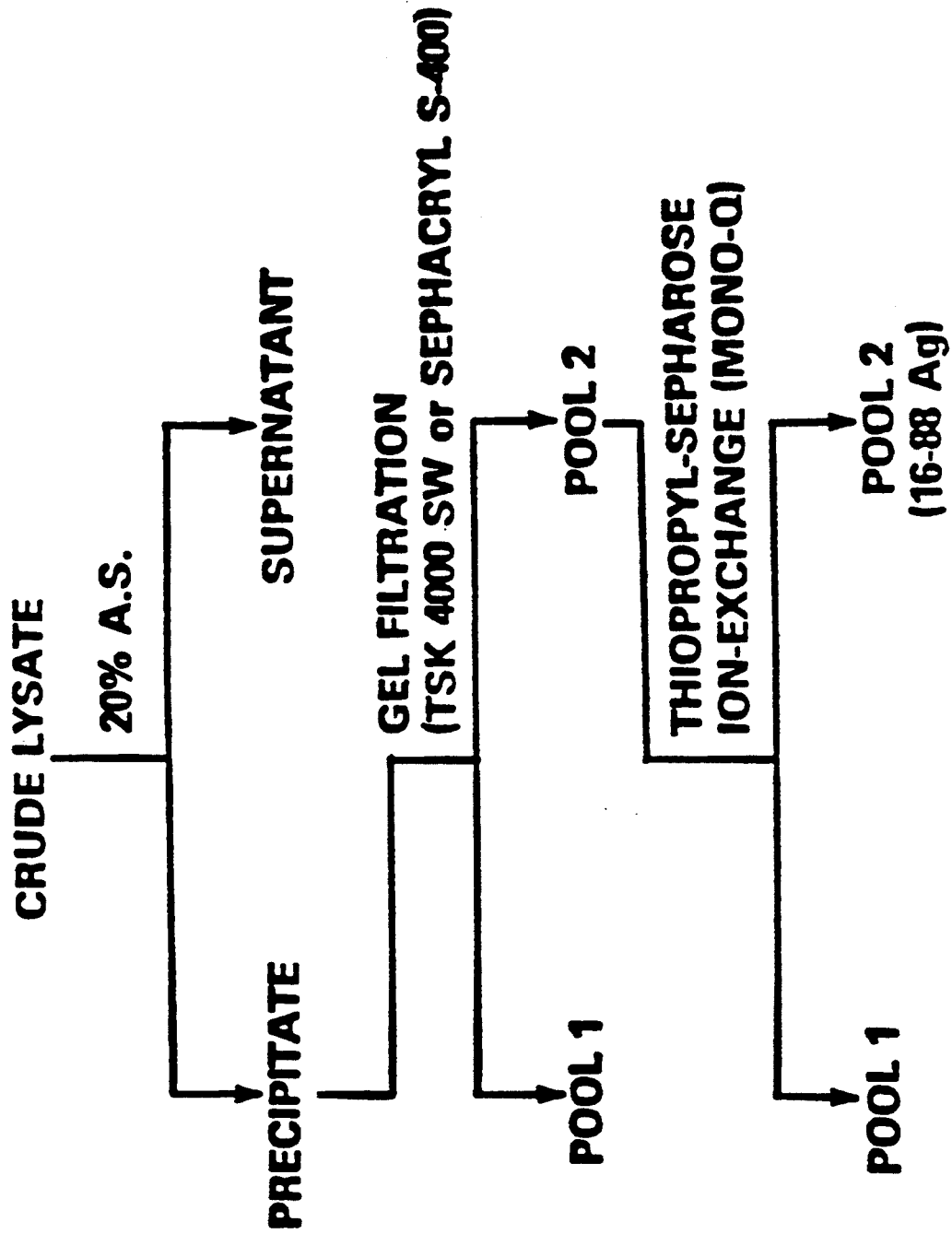

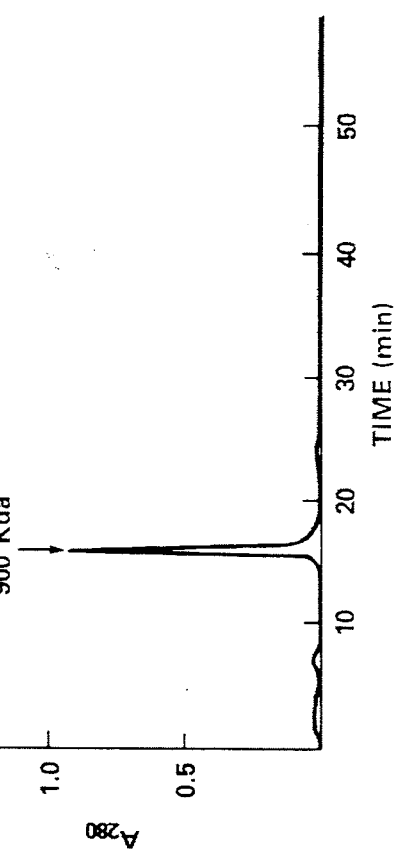
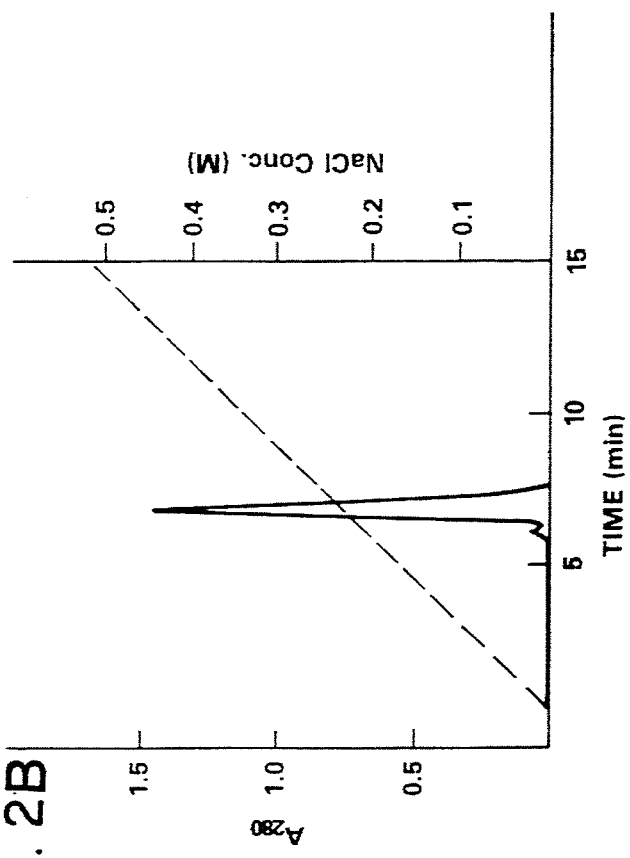

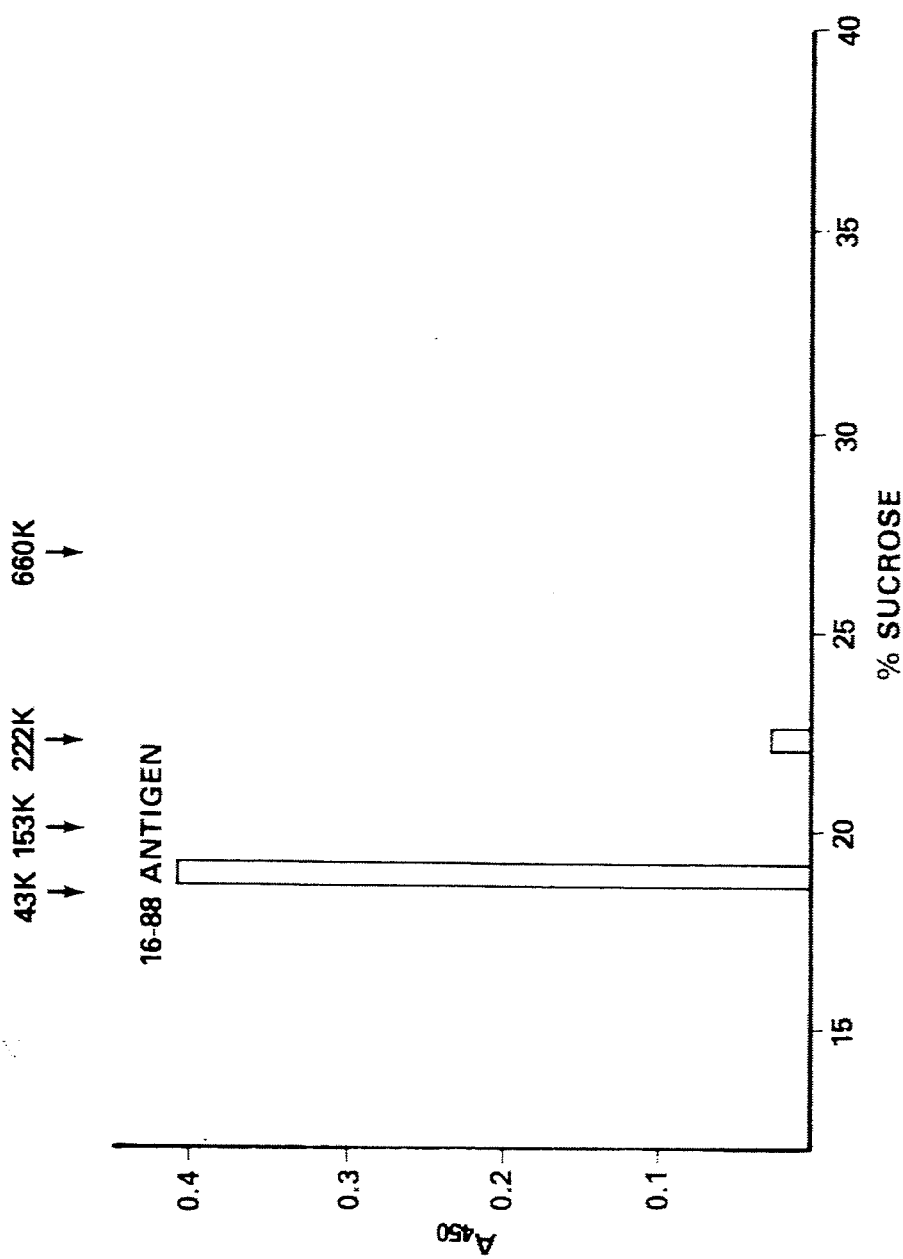

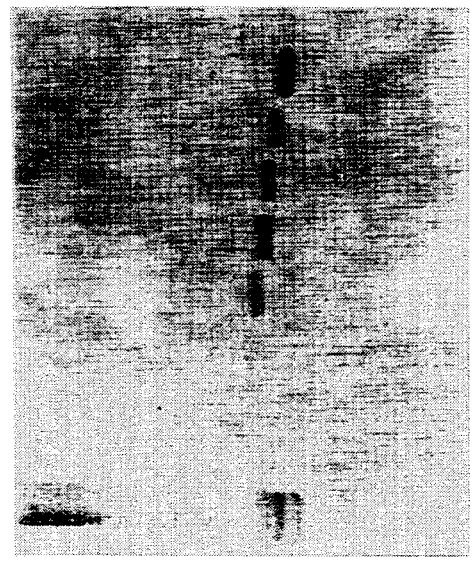
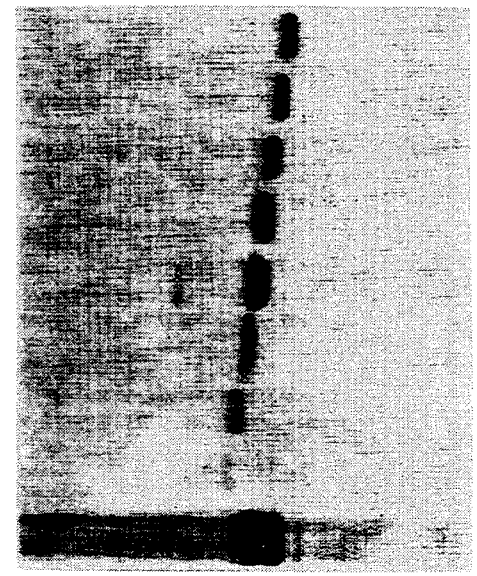
FIG. 7

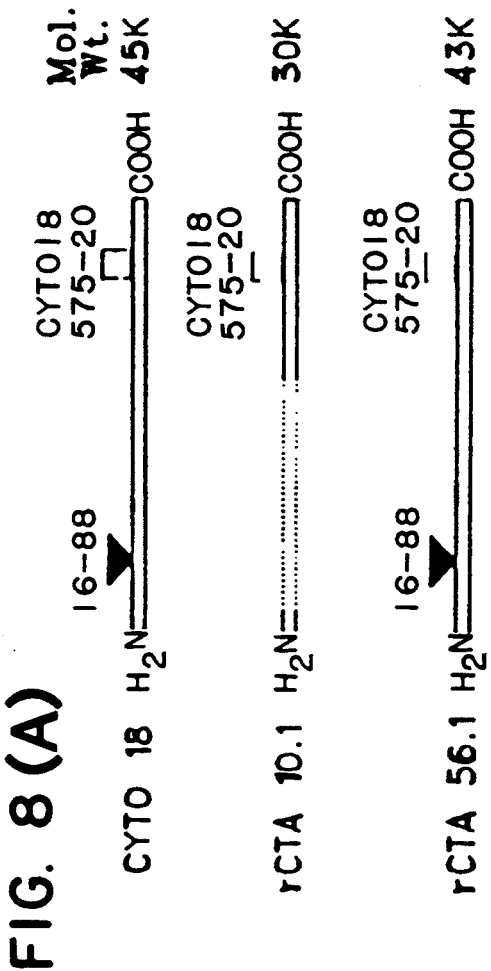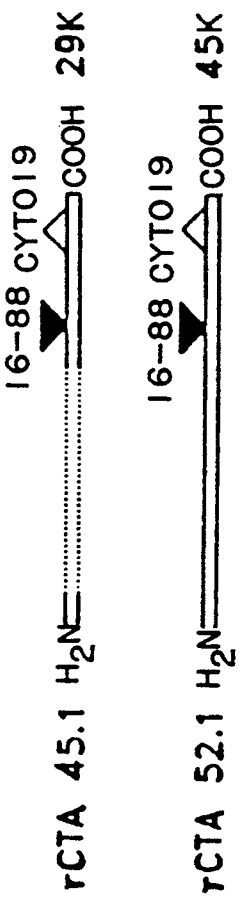
FIG. 8(A)
FIG. 8(B)

ANTIGEN RECOGNIZED BY MCA 16-88

This is a continuation of application Ser. No. 07/343,475 filed Feb. 28, 1989, now abandoned, which is the National Phase of PCT/US88/02245, filed Jul. 1, 1988, is a continuation-in-part of U.S. Ser. No. 07/069,478, filed Jul. 2, 1987, now abandoned.

BACKGROUND OF THE INVENTION

Colorectal cancer is the second most prevalent cancer in the United States, affecting both men and women. Until recently, the only viable treatment for this disease has been surgery, which has a poor prognosis for patients with transmural extension of tumor and metastasis to regional lymph nodes. A dramatically improved prognosis was indicated in a recently reported randomized Phase II-active specific immunotherapy trial, which showed that immunization of patients with autologous tumor cells admixed with Tice BCG (Bacillus Calmette Guerin) (Institute for Tuberculosis Research, Chicago, Ill.) significantly increased delayed cutaneous hypersensitivity responses and, over a four year period of time, significantly decreased recurrence and mortality (3).

There have been numerous publications describing the identification of colon carcinoma-associated antigens (4–9). The majority of these antigens were identified using monoclonal antibodies generated by immunizing mice with some form of the colon tumor (extracts, dissociated cells, membrane preparations, and etc.) or colon tumor cell lines. These mouse antibodies identify a repertoire of antigens that were deemed to be antigenic in the mouse. In addition to these studies there are several reports of human monoclonal antibodies that show specific reactivity with tumor material (19).

Using peripheral blood B-cells from colorectal patients actively immunized with autologous tumor cells and BCG in immunotherapy protocols, we have successfully developed a strategy for producing human anti-tumor monoclonal antibodies (1). Unlike mouse monoclonal antibodies generated against human colon cancer, which often recognize tissue components also found in healthy individuals, such as CEA, our human monoclonal antibodies exhibit no reactivity with CEA, blood group determinants or histocompatibility antigens, indicating that these antibodies are characterized by a specificity confined to those epitopes that are recognized as immunogenic in the autologous host.

We have used these human monoclonal antibodies as probes to identify tumor antigens. We have identified a particular antigen in colon tumors, extracts of colon tumor cell lines and human tumor xenografts generated in nude mice. The subject antigen is characterized by containing an epitope recognized by human monoclonal antibody (MCA) 16-88, which has been detected in approximately 60% of all colorectal tumors. We have found that the epitope identified by human MCA 16-88 is not recognized by mouse monoclonals, even those generated by immunizing mice with the human antigens containing this epitope.

SUMMARY OF THE INVENTION

The present invention comprises the epitope recognized by the human monoclonal antibody 16-88, the human tumor antigen containing this epitope, which we have identified, isolated and characterized, and anti-idiotypic antibodies to human MCA 16-88, which comprise the same epitope. The invention also relates to the use of antibodies to the antigen containing this epitope for diagnosis and monitoring of treatment of cancer and to the use of this antigen in the preparation of vaccines to elicit an immune response similar to that obtained against tumor cells containing this epitope.

BRIEF DESCRIPTION OF THE DRAWINGS

FIG. 1 is a flow chart summarizing the purification scheme of antigen recognized by human MCA 16-88.

FIG. 2 shows isolation of antigen recognized by human MCA 16-88.

FIG. 2A shows the analysis of purified antigen by HPLC Gel filtration.

FIG. 2B shows the analysis of purified antigen by anion exchange HPLC and

FIG. 2C shows isolation of the purified antigen by isoelectric focusing.

FIGS. 5, 6 and 7 illustrate the characterization of the antigen by native gradient PAGE, sucrose density gradient centrifugation and SDS-polyacrylamide gel electrophoresis, respectively.

FIG. 8A represents the reactivity of the 16-88 antibody and anti-cytokeratin 18 antibody with recombinant antigens.

FIG. 8B represents the reactivity of the 16-88 antibody and anti-cytokeratin 19 antibody with other recombinant antigens.

DESCRIPTION OF THE PREFERRED EMBODIMENTS

Figure 4:
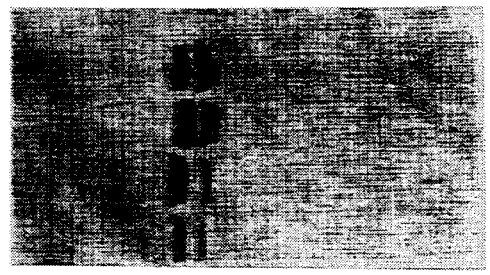
FIGS. 3 and 4 show SDS-PAGE and Western Blot purification of the antigen.

We have found the antigen containing the epitope recognized by human MCA 16-88 in approximately 60% of the colon tumors examined (10). We have also found the colon carcinoma cell lines HT-29, SW1463, SW948, SW403, LS174, LoVo and WiDr (ATCC, Rockville, Md.) to contain the same antigen. Because of the low reactivity of human MCA 16-88 with matched normal colonic tissue, it is evident that this antigen is preferentially expressed in colon tumor cells.

In addition, we have detected this antigen in colon cancer patients' sera, while sera from normal individuals exhibited no detectable antigen levels. Interestingly, some patients with demonstratable tumor burden had low CEA levels but did have high levels of antigen recognized by human MCA 16-88, while other had low but detectable levels of antigen with significant amounts of CEA. The antigen containing the epitope recognized by human MCA 16-88 is complimentary to CEA in its usefulness as a tumor marker, as it is not found in detectable levels in the sera of healthy individuals or in normal tissue. Accordingly, it will be an invaluable tool as an immunoreagent for diagnosis and monitoring whether used alone or in combination with other tumor antigens (11). It can also be used in vaccines to stimulate humoral/host responses (12,13).

Human MCA 16-88 proved to be a valuable probe for the isolation and biochemical characterization of this antigen. However, in certain instances it was necessary to use the mouse monoclonal antibodies 575-20 and 810-12 we prepared, which recognize different epitopes on the same antigen.

Purification of the antigen was achieved by salt precipitation, gel filtration chromatography and affinity chromatography. The purified antigen migrated as a single protein on native gradient polyacrylamide gel electrophoresis (native PAGE) and as a series of closely migrating proteins by denaturing gradient polyacrylamide gel electrophoresis under reducing conditions.

The molecular weight of the native protein was indicated to be approximately 900K by gel filtration and 100–140K by native PAGE. The different molecular weights indicate that either the shape of the molecule is not that of a globular protein or that some non-protein material (e.g., lipid) is associated with the protein. These conclusions were supported by sucrose density centrifugation of the native antigen, which indicated a size of slightly greater than 43K. Thus, the apparent size of the native molecule as determined by its density also suggests a non-globular protein shape or the association of the antigen with a non-protein component.

The molecular weight determination by SDS-PAGE under reducing conditions of the antigen resulted in a series of closely migrating proteins in the range of 43K to 35K.

Experiments involving intrinsic labeling of the antigen with $^3$H glucosamine indicate that this protein has little or no carbohydrate attached. In addition, it does not appear to be sulfated as attempts to incorporate $^{34}SO_4$ into the protein were not successful. $^{32}PO_4$ was incorporated, however, indicating that the protein is phosphorylated.

We have isolated this tumor associated antigen by its reactivity with the 16-88 human monoclonal antibody. Based on the presence of this antigen in various colon carcinoma and as well as in sera from various colon cancer patients, it is a significant antigen for diagnostic purposes and for vaccine development. It is defined and clearly identified by both its immunoreactivity with human MCA 16-88 and by its isoelectric focusing point.

Using the human monoclonal antibody 16-88, we have probed an E. coli expression library for production of recombinant proteins exhibiting the MCA 16-88 epitope (20). Five positive clones have been analyzed in detail. One series of clones (FIG. 8A) are derived from the cDNA for human cytokeratin No. 18. This has been confirmed by DNA sequence analysis and comparison with the published sequence (21). The important conclusion from this study is that the region of the cytokeratin No. 18 gene sequenced by Romano et al and expressed in clones rCTA 10.2 and rCTA 12.1 does not comprise the human MCA 16-88 defined epitope. This epitope is contained within the amino terminal portion of cytokeratin No. 18 as defined by rCTA 56.1.

In addition to reactivity towards cytokeratin No. 18, the MCA 16-88 defined epitope is expressed on other members of the cytokeratin family. An example of this is shown in FIG. 8B. Analysis of rCTA 45.1 and rCTA 52.1 with specific antisera has identified this as recombinant cytokeratin No. 19. Two of the gene products carrying the MCA 16-88 defined epitope have been shown to the members of the cytokeratin family. These represent only two of the several closely migrating proteins defined by the biochemical analysis. Clearly, the important epitope defined by MCA 16-88 is distinct from other more restricted epitopes within the intermediate filament family of proteins (Table 3).

The tumor associated antigen recognized by MCA 16-88 was purified from HT-29 cell lines. The antigen appears to be related to cytokeratins 8, 18 and 19 because the epitope recognized by the human monoclonal antibody 16-88 is found on these molecules and because epitopes recognized by mouse monoclonal antibodies specific for cytokeratins 8, 18 and 19 are reactive with this antigen. The antigen differs from cytokeratins 8, 18 and 19 (the only cytokeratins reported to be present in HT-29 cells) by its solubility in aqueous solution (unlike native cytokeratins 8, 18 and 19) and its smaller molecular size range. In addition, N-terminal protein sequence data of two of the polypeptides in the antigen complex indicate a different amino acid sequence for this antigen than that reported for cytokeratins 8, 18 and 19.

In addition to the purification of the antigen, we have further characterized the MCA 16-88 reactivity with the isolation of mouse anti-idiotypic monoclonal antibodies (Table 2).

PURIFICATION OF THE ANTIGEN RECOGNIZED BY MCA 16-88

A flow chart summarizing the purification scheme of the antigen recognized by human MCA 16-88 is presented in FIG. 1. Extraction of the tumor cell line. HT-29, in a buffer containing the detergent NP-40 (Sigma Chemical Co.) resulted in an aqueous solution, which, after clarification, contained an antigen recognized by the human MCA 16-88. This protein, after dialysis, was precipitated with 20% ammonium sulfate (A.S.). After centrifugation, the redissolved precipitate was fractionated on a TSK 4000SW gel filtration column.

Figure 3:
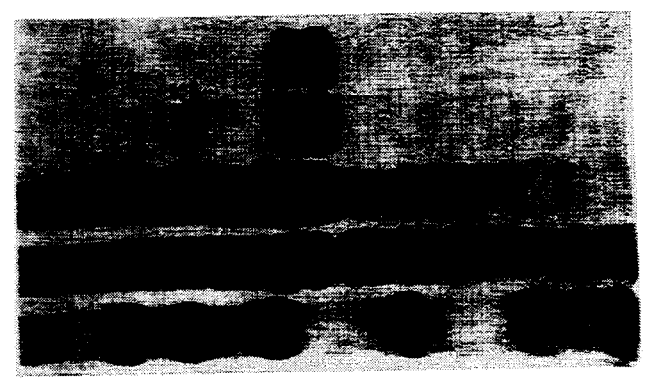

The antigen pool from the gel filtration column was applied directly to a thiopropyl-Sepharose 6B column and eluted with 10 mM dithiothreitol. FIGS. 3 and 4 show the SDS-PAGE and the Western blot analysis of the antigen pools during purification. Lanes A–E show Coommassie blue staining after SDS-polyacrylamide gel electrophoresis; F–I, Western blot analysis using MCA 16-88 as a probe; Lane A, SDS molecular weight standards; Lanes B and F, crude extract; Lanes C and G, 20% ammonium sulfate precipitate; Lanes D and H, TSK 4000 gel filtration chromatography; and Lanes E and I, thiopropyl-Sepharose chromatography.

ANTIGEN CHARACTERIZATION

Purity of the Native Antigen

The purity of the nondenatured antigen was assessed by size exclusion HPLC, anion exchange HPLC and agarose IEF. The results show that single peaks were obtained using analytical HPLC and a single band at an isoelectric pH of 5.3±0.3 was obtained by analytical IEF (FIG. 2). Thus the native antigen has the characteristics of a nearly homogeneous protein based on these criteria. FIG. 2 represents the analysis of purified antigen by HPLC gel filtration, anion exchange HPLC and isoelectric focusing.

A. A Zorbax GF-450 column (9.4 mm×25 cm) (DuPont) was equilibrated in PBS, calibrated with molecular weight standards and then used for resolution of purified antigen.

—$A_{280\ nm}$

B. A Pharmacia Mono Q column (5 mm×5 cm, anion exchange) was equilibrated in 20 mM Tris, pH 8.0 (Buffer A). A sample of purified antigen was loaded. The column was developed with a linear gradient from buffer A to buffer A+1.0M NaCl.

—$A_{280\ nm}$

- - - NaCl Concentration

Molecular Weight Characteristics

The molecular weight the of native antigen as determined by gel filtration column chromatography was found to be approximately 900K by size exclusion column chromatography (FIG. 2B). This molecular weight was confirmed on other gel filtration matrices, such as Fratogel HW55F-65F and Sephacryl S-400. FIG. 5 indicates a molecular weight of approximately 100–400K when determined by native gradient PAGE. This difference in molecular weights when measured by the different methods remained even when the native gradient PAGE buffer (0.1M Tris, 0.1M boric acid, pH 8.3) was used in the gel filtration system and when a non-borate containing buffer (0.05M Tris 0.5M Glycine, pH 8.3) was substituted in the native PAGE system.

The difference in molecular weight between gel filtration and gel electrophoresis indicated that the shape of the antigen recognized by MCA 16-88 is not globular, as presumed for molecular weight determination by gel filtration. To generate information about the shape of this molecule, sucrose density gradient centrifugation was performed. FIG. 6 shows that the antigen had the characteristics of a protein slightly larger than 43K with regard to its density in its native form.

SDS-Polyacrylamide Gel Electrophoresis

In FIG. 7 the antigen appears as a series of polypeptide bands between 43K and 35K molecular weight, as determined by SDS-PAGE under reducing conditions. The protein bands were immunoreactive and could be separated by electro-elution following SDS-PAGE. Neither the pattern, location, nor the immunoreactivity of these bands was changed in the same system using non-reducing conditions.

Lanes 1–9 show Coommassie blue staining after SDS polyacrylamide gel electrophoresis; Lanes 10–18, Western blot analysis using MCA 16-88 after SDS-polyacrylamide gel electrophoresis; Lanes 1 and 10, 20% ammonium sulfate precipitate; Lanes 2 and 11, electro-eluted protein band A; Lanes 3 and 12, electroeluted protein band B; Lanes 4 and 13, electroeluted protein band C; Lanes 5 and 14, electroeluted protein band D; Lanes 6 and 15, electroeluted protein band E; Lanes 7 and 16, electroeluted protein band F; Lanes 8 and 17, electroeluted protein band G; and Lanes 9 and 18, electroeluted protein band H.

Biosynthetic Labeling

As illustrated in the Examples, in vivo labeling of HT-29 cells was attempted using $^3H$ Glucosamine, $^{35}SO_4$ and $^{32}PO_4$. A mouse monoclonal antibody against the antigen was used for immunoprecipitation because the antigen could not be precipitated with human MCA 16-88 as it is an IgM molecule. Little or no incorporation of $^3H$ Glucosamine or $^{35}SO_4$ was observed in these experiments. However, labeling of the antigen did occur when $^{32}PO_4$ was used, indicating that this protein is phosphorylated.

Isoelectric Focusing

Purified antigen recognized by human MCA 16-88 was subjected to isoelectric focusing in 1% agarose gels. The antigen appeared as a single band at an isoelectric point of about pH 5.5 (FIG. 2C).

Cloning of Recombinant Antigens Recognized by MCA 16-88

A library of lambda ORF8 phage (20) carrying cDNA prepared from the cell line HT29 was probed with MCA 16-88 and mouse MCA 575-20. A total of 160,000 recombinant phage (with 74% cDNA inserts) were screened. Two clones reactive with MCA 575-20 were isolated and characterized, e.g. rCTA 10.0, (FIGS. 8A and Table 3). Three clones reactive with MCA 16-88 were also isolated. Characterization of clones rCTA 56.1, 45.1 and 52.1 is included in FIG. 8 and Table 3.

Antigen Detection in Patients' Sera

A panel of patients' sera was screened for the antigen recognized by human MCA 16-88, as well as monitored for CEA and PHAP levels. The results of these tests can be seen in Table 1. The levels of antigen in the sera tested did not correlate with high CEA and PHAP levels, but did appear to be complementary to them.

Recognition of Antigen by Mouse Monoclonal Antibodies

Several mouse monoclonal antibodies were derived which showed immunoreactivity with the antigen recognized by MCA 16-88. Among these, the mouse monoclonals 575-20 and 810-12 recognized this antigen, and competitive assays demonstrated that none of them reacted with the specific epitope recognized by human MCA 16-88 (Table 4).

Reactivity of Antigen Recognized by MCA 16-88 with Antibodies to Intermediate Filament Proteins The antigen complex consists of closely related polypeptides in the molecular weight range of 43–35K which are smaller than all of the previously described cytokeratins except cytokeratin 19, which has a molecular weight of 40K. Eight bands from the antigen complex, labelled A–H, were electroeluted and subjected to analyses by Western blot and EIA. As can be seen in Table 5, MCA 16-88 recognized bands B–H. Anti-cytokeratin 8 recognized bands A–H, anti-cytokeratin 18 recognized only bands B–F, and anti-cytokeratin 19 recognized only bands E–H. The murine MCA (MCA 575-20), made by immunizing mice with purified antigen reacts to bands A–G. This finding suggests that this murine MCA reacts to a different epitope from MCA 16-88. This was confirmed by competition radioimmunoassay using $^{125}I$-labeled MCA 16-88. The Western blot results were confirmed by EIA with each of these polypeptides. These data demonstrate that epitopes recognized by monoclonal antibodies specific to cytokeratins 8, 18, and 19 are found on antigen.

EIA Characterization of Antigen Recognized by MCA

Table 6 summarizes the characterization of the antigen with a panel of monoclonal antibodies specific for various intermediate filament proteins and the reactivity of MCA 16-88 to a panel of purified intermediate filament proteins.

The monoclonal antibodies specific for cytokeratin 8, 18, and 19 and the murine monoclonal antibody, MCA 575-20, were the only antibodies reactive with the antigen. The reactivity of MCA 575-20 was the same to the antigen and cytokeratin 18 but did not react to the other intermediate filament proteins. The reactivities of anti-cytokeratins 8 and 18 are higher for the antigen than for the purified cytokeratins. This could be due to epitopes exposed on the antigen that are not as readily accessible on the intact cytokeratin. Thus, the antigen has epitopes shared with cytokeratin 8, 18 and 19. In addition, the human MCA 16-88 recognizes epitopes on the antigen, cytokeratins 8, 18, and possibly desmin, but not vimentin.

Recognition of Antigen by Anti-Idiotypic Mouse Monoclonal Antibodies

Several mouse monoclonal antibodies were derived which showed direct competition with the antigen for binding the MCA 16-88. Table 2 presents the reactivity of these anti-idiotypic antibodies.

Location of 16-88 Epitopes

The human monoclonal antibody 16-88 recognizes epitopes that are contained in the intermediate filament proteins cytokeratin 18 and desmin in Western Blots using purified proteins. The 16-88 monoclonal also stains lymphoid cells isolated from peripheral blood by ficoll-hypaque and fixed with ethanol. Since these cells do not contain keratin, but do contain other intermediate filament proteins this provides indirect evidence that 16-88 recognizes an epitope shared by at least 3–4 gene products included in the family of cytoskeletal protein known as intermediate filaments including but not limited to cytokeratin 8, 18, and desmin.

Sequence Analysis of Antigen Recognized by MCA 16-88

N-terminal protein sequence analysis was obtained from bands G and H (lanes 8 and 17 and lanes 9 and 18, respectively, in FIG. 7), which were electroeluted after SDS-PAGE analysis. Protein sequencing was performed on an automated Applied Biosystems, Inc. gas phase sequencer. These results indicate that although bands G and H differ in size, they have the same N-terminal protein sequence. When comparisons to known protein sequences were performed it was found that these polypeptides of the antigen recognized by MCA 16-88 have some homology with cytokeratins 8 and 19 (approximately 20%). However, they are not identical with these cytokeratins and essentially no homology was found with cytokeratin 18. Although this antigen shares epitopes with cytokeratin 8, 18 and 19, it clearly represents a different protein.

The eight closely migrating bands A–H (lanes 1–9 and 11–18 in FIG. 7) are subunits of the antigen recognized by human MCA 16-88. The N-terminal ends of bands G and H are as follows:

```
                        10
G: V L E V D P N I Q A V R T Q X K X X I X T L N N K
                        10
H: V L E V D P N I Q A V R T Q E K X Q I K T L N X X F
   A S F
```

In the above sequences, X represents and undetermined amino acid.

ATCC Deposits

A human B-cell derived cell line producing the human monoclonal antibody MCA 16-88 was deposited with the American Type Culture Collection (ATCC) at 12301 Parklawn Drive, Rockville, Md. 20852, U.S.A. under Budapest Treaty requirements on Jan. 30, 1984, and given the accession number HB 8495.

Murine hybridoma cell lines MID 95, MID 268, and MID 65-6 were deposited with the ATCC under Budapest Treaty requirements on Jul. 2, 1987, and given accession numbers HB 9470, HB 9471 and HB 9472, respectively.

Murine hybridoma cell lines 575-20 and 810-12 were deposited with the ATCC under Budapest Treaty requirements on Jun. 30, 1988.

EXAMPLES

Cell Lines

Human colonic adenocarcinoma cell line, HT-29, was obtained from the American Type Culture Collection (ATCC), Rockville, Md. Cells were cultured in Dulbecco's Modified Eagle's medium supplemented with 10% fetal bovine serum. The cells were incubated at 37° C. in an atmosphere of 5% $CO_2$.

Production and Purification of Human MCA 16-88

The diploid cell line producing the human monoclonal antibody 16-88 was grown in hollow fiber cartridges in the presence of RPMI 1640 supplemented with 10% fetal bovine serum. The antibody (human IgM) was purified by gel filtration and ion exchange chromatography.

Development of Mouse Monoclonal Antibodies

Balb/c mice (6–8 weeks old) were immunized with 50 μg of purified antigen from HT-29 cell in complete Freund's adjuvant. Two additional antigen immunizations were given with incomplete adjuvant. Three days before fusion, mice were immunized with 50 mg of antigen in PBS. Splenic lymphocytes were fused with mouse myeloma NS-1 (ATCC) (3:1 ratios) as previously described (11). Supernatants were screened by EIA against purified antigen. Positive cultures were expanded and cloned by limiting dilution.

Development of Anti-iodiotypic Mouse Antibodies MID65, MID95 and MID268

Balb/c mice were injected with 25 μg human IgM (Miles) IV, 25 μg human IgM intraperitoneally. Three days later, mice were injected with 200 μg/kg cyclophosphamide (Sigma) followed by two additional cyclophosphamide injections at two day intervals. Mice were then immunized with 50 μg purified 16-88 antibody (pool 160): once in complete Freund's adjuvant (Gibco) and two weeks later in incomplete Freund's adjuvant (Gibco). One mouse was chosen on the basis of high serum reactivity to 16-88 and low reactivity to IgM. Three days prior to fusion the mouse was boosted with 50 μg 16-88 (pool 141) in PBS. Splenic lymphocytes were fused with mouse myeloma NS-1 (ATCC) using PEG at 3:1 ratio. Cultures which tested positive in 16-88 competition assays but did not bind IgM were expanded and cryopreserved. Additionally, MID65, MID95 and MID268 did not bind 16-52 antibody (derived from the same patient lymphocytes as 16-88).

$^3H$ Glucosamine Labeling of HT-29 Cells

HT-29 cells were grown in flasks containing RPMI 1640 supplemented with 10% fetal calf serum (Gibco, Inc.). After washing with the RPMI 640, the cells were placed in RPMI 1640 without glucose, supplemented with 9% dialyzed, heat-inactivated fetal calf serum and 1% heat-inactivated fetal calf serum and incubated for 60 min at 37° C. This medium was then replaced with medium containing 0.05 mCi/ml $^3$H glucosamine (ICN) and incubated for 16 hours at 37° C. The $^3$H glucosamine-containing medium was removed and the cells were washed several times with PBS and extracted with lysis buffer as described below.

$^{32}$Orthophosphate Labeling of HT-29 Cells

HT-29 colon carcinoma cells were labeled with $^{32}$P orthophosphate as described previously (22). Briefly, $2 \times 10^7$ cells were washed, twice with 50 mM HEPES containing 0.01% bovine serum albumin (BSA, Sigma), pH 7.5. The cells were then cultured for 15 min in phosphate free media (High Glucose EMEM, Irvine Scientific, Santa Anna, Calif.) then pulsed with 500 $\mu$Ci $^{32}$p orthophosphate (NEN Research Products), for 3 hours at 37° C. under 6% $CO_2$. After labeling, the cells were washed twice with ice cold PBS containing 100 mM sodium fluoride, 100 mM sodium pyrophosphate, and 1.0 mM EDTA pH 7.4 and solubilized as described above.

$^{35}$S Sulfate Labeling of HT-29 Cells

For labeling with $^{35}$S sulfate, $2 \times 10^7$ cells were washed twice with Hams F-12 (Gibco) and preincubated for 30 minutes at 37° C. under 6% $CO_2$ in Hams F-12 containing 10% dialyzed PBS. Then, 500 $\mu$Ci $^{35}$S sulfate (NEN Research Products), was added and the cells were cultured for 18 hours at 37° C. under 6% $CO_2$, at which time they were solubilized and precleared as described above.

Immunoprecipitation of Antigen

Immunoprecipitation was performed with the mouse monoclonal antibody produced as described above, which were designated 575-20 (IgG1). 50 ml aliquots of $^3$H glucosamine-labeled extract was mixed with 50 mg of the antibody and kept at 23° C. for 30 min. Antigen-antibody complexes were precipitated by incubation with 200 ml of a 10% solution of formalin-fixed *Staphylococcus auereus* protein A at 4° C. for 16 hours. After centrifugation at 20,000×g for 5 min, the precipitate was washed several times and the treated with SDS-PAGE sample buffer.

Extraction of Antigen Recognized by Human MCA 16-88

Frozen HT-29 cells were mixed with extraction buffer (50 mM Tris, pH 7.5+150 mM NaCl+5 mM EDTA+0.1 mM PMSF+0.5% NP40). The cells were stirred at 4° C. for 60 min. The mixture was then centrifuged at 100,00×g for 60 min. at 4° C. The resultant precipitate was discarded and the clarified supernatant was withdrawn and subjected to further purification.

Salt Precipitation of Antigen Recognized by Human MCA 16-88

The clarified supernatant from extracted HT-29 cells was maintained at 4° C. and made up to 20% ammonium sulfate using a saturated solution. The mixture was stirred at 4° C. for 60 min. It was then centrifuged at 40,000×g for 30 min. at 4° C. The supernatant was removed and the pellet comprising the relevant antigen was redissolved in a small volume of gel filtration buffer (25 mM Tris-HCl, pH 6.8).

Gel Filtration Chromatography

A TSK 4000SW (2.5×60 cm) (Toyo Soda) HPLC column, equilibrated in gel filtration buffer, was used for the chromatographic separation of the ammonium sulfate precipitates antigen. The antigen was loaded onto the column and eluted at a flow rate of 4.0 ml/min. Fractions containing the antigen were pooled for the next purification step. Other gel filtration matrices such as Fractogel HW (Toyo Soda), Zorbax GF-450 (DuPont) or Sephacryl S-400 (Pharmacia, Inc.) were found to be suitable replacements for the TSK 4000SW column.

Thiopropyl-Sepharose 6B Chromatography

Thiopropyl-Sepharose 6B (Pharmacia, Inc.) was washed and equilibrated in phosphate buffered saline. The sample from the gel filtration column was loaded onto the column at slow flow rate (15 ml/hr). The column was washed with PBS follow by PBS+1.0M NaCl, until no further protein could be eluted. The antigen was then eluted with 10.0 mM dithothreitol (DTT) in 0.3M sodium bicarbonate, pH 8.4 and 1.0 mM EDTA. The purified antigen pool was dialyzed against 25 mM Tris-HCl, pH 7.5 and stored at −20° C.

Polyacrylamide Gel Electrophoresis

SDS-polyacrylamide gel electrophoresis was performed as previously described (12). The gel composition made use of both homogeneous and gradient gels. Native gradient gel electrophoresis was carried out as previously described (13).

Isoelectric Focusing

Isoelectric focusing of the antigen recognized by human MCA 16-88 was carried out in 1% agarose gels (25×125×0.5 mm) containing ampholines in a pH range of 3.5–10.0. After 60 min of prefocusing at 1500V, 15W, 10 mA, and 10° C., samples were applied and focusing was performed under the same conditions for 120 min. After focusing, proteins were fixed by immersing the gel in 20% TCA for 30 min. The gel was stained for 15 min in 0.25% CBB R280 in 40% ethanol, 10% acetic acid and destained in 40% ethanol, 10% acetic acid. The following proteins were used as pI markers: C-Phycocyanim (4.75; 4.85), Azurim P (5.0, 6.0), trifluoroacetylated myoglobin Met (6.86), myoglobin met (6.46), myoglobin Met E (7.30).

Western Blot Analyses

Western blot analyses of various antigen pools were performed as described by Towin (14). Nitrocellulose sheets to which proteins had been transferred were blocked with blotto, probed with a primary antibody, either human MCA 16-88 or mouse monoclonal antibodies to the antigen (mouse MCA 16-88), and further reacted with a peroxidase-labeled second antibody of either goat anti-human IgM or goat anti-mouse Ig (G, A, M) [KPL, Rockville, Md.] to generate an appropriate signal. The substrate used was dimethylamino benzidine (DAB) and hydrogen peroxide made up to 0.06% and 0.003% respectively in PBS.

Detection of Antigen by EIA

We developed two types of EIA for detection of antigen. In the first assay, the human MCA 16-88 was used to identify the antigen. HT-29 protein extract solution containing antigen was coated onto microtiter plates at appropriate dilutions (e.g., starting at 10 ug/ml) in PBS, at either 4° C. for 16 hours or 23° C. for 2 hours. The protein solution was removed and washed 2X with PBS+0.05% Tween-20. The unreacted sites on each well were blocked with blotto (5% non-fat dry powdered milk in PBS) in 0.05% Tween-20 by incubating at 23° C. for 60 min. After washing, the wells were reacted with the primary antibody human MCA 16-88 (1.0 ug/ml) diluted into blotto and incubated a 23° C. for 60 min. After removal of the primary antibody and washing, the wells were treated with an appropriate dilution (1:30,000) of peroxidase-labeled goat anti-human IgM (KPL) for 60 min at 23° C. After removal of the anti-human conjugate and several washes, the wells were treated with the peroxidase substrate (0.006% tetramethylbenzidine and 0.0007% urea peroxidase in 0.5M sodium acetate, pH 5.5).

The second assay made use of two of the mouse monoclonal antibodies developed against this antigen: 810-12 and 575-20. The 810-12 mouse MCA 810-12 was coated onto plates at 3 mg/ml in PBS at 4° C. for 16 hours. After washing, the wells were blocked (3% fish gelatin in PBS) for 45 min at 23° C. After washing, the wells are incubated with test sera containing the antigen and then coated with peroxidase-labeled mouse MCD 575-20 and incubated for 60 min at 37° C. After washing several times with 1% glycerol containing 0.05% Tween-20, the wells were treated with substrate as described above. Absorbance was determined at 450 nm.

Sucrose Density Gradients

Linear 10-40% sucrose gradients were formed in the presence of PBS in centrifuge tubes. Standard proteins or purified antigen recognized by human MCA 16-88 were layered onto the gradients in each tube, and all tubes were centrifuged at 40,000 r.p.m. and 4° C. for 17 hours in a Beckman SW41 rotor. The contents of each tube were fractionated and the relative molecular size of the antigen was determined by measuring either the absorbance at 280 nm or the reactivity with human MCA 16-88 by EIA.

REFERENCES

1. Silverberg, E., CA (1983) 33:9-25.
2. Goligher, J. C., Surgery of the Anus, Rectum and Colon, 4th ed., London: Baillere Tindall (1980) 47-471.
3. Hoover, H. C., Jr., et al. Cancer (1985) 55:1236-1243.
4. Gold, P. and Freedman, S. O., *J. Exp. Med.* (1985) 122:467-481.
5. Yeoman, L. C. et al., Human Colon Tumor Antigens, In: H. Busch and L. C. Yeoman (eds.), Vol. 19, 231-271, New York: Academic Press, Inc. (1982).
6. Magnani, J. L. et al., *Cancer Res.* (1983) 43:5489-5492.
7. Artigas, C. et al., *Cancer Res.* (1986) 45:1874-1881.
8. Blaszczyk, M. et al., *Cancer Res.* (1984) 44:245-253.
9. Ross, A. N., et al., *Biochem. Biophys. Res. Comm.* (1986) 135:297-303.
10. Haspel, M. V. et al., *Cancer Res.* (1985) 45:3951-3961.
11. Bowser-Finn, R. A., et al.
12. Shinnick, T. M., et al., Synthetic peptide immunogens as vaccines, In: *Annual Review of Microbiology*, L. N. Ornston (ed.), Vol. 37, Palo Alto, Calif., Annual Review, Inc. (1983).
13. Norrby, E. et al., *J. Virol.* (1986) 58(2):536-541.
14. Touitou, I. et al. *Biochimie* (1985) 67:1257-1266.
15. Probhakas, B. S. et al., Monoclonal Antibody Techniques Applied to Viruses. In: *Methods in Virology*, K. Macamorosh and H. Kaprowski (eds.), Vol. 7, New York: Academic Press, Inc. (1984).
16. Laemmli, U. K., *Nature* (London) (1970) 227:680-685.
17. Lambin, P. and Fine, J. M., *Anal. Biochem.* (1979) 98:160-168.
18. Towbin, H. et al., *Proc. Natl. Acad. Sci. U.S.A.* (1979) 76:4350-4354.
19. Cote, R. J., et al., *Proc. Natl. Acad. Sci. U.S.A.* (1986) 83:2959-2963.
20. Meissner, P. S. et al., *Proc. Natl. Acad. Sci. U.S.A.* (1987) 84:0000-0000.
21. Romano, V. et al., *Diff* (1986) 30:244-253.

We claim:

1. An essentially pure human tumor cell soluble protein antigen comprising the human tumor cell epitope to which human monoclonal antibody 16-88 binds, found on a tumor associated antigen expressed by colon carcinoma cell lines HT-29, SW1463, SW948, SW403, LoVo and WiDr, said antigen comprising a soluble protein having a molecular weight of approximately 900K when determined by gel filtration column chromatography, a molecular weight of approximately 100-140K when determined by native gradient polyacrylamide gel electrophoresis, and an isoelectric focusing point of about pH 5.5, and which migrates as soluble peptides of approximately 35K to 43K when subjected to sodium dodecyl sulfate polyacrylamide gel electrophoresis performed under reducing conditions, said antigen further comprising epitopes to which monoclonal antibodies to cytokeratin 8 bind and to which monoclonal antibodies to cytokeratins 18 and 19 bind, but not to which antibodies to vimentin bind.

2. An essentially pure soluble peptide subunit of the human tumor cell antigen of claim 1, comprising the human tumor cell epitope to which human monoclonal antibody 16-88 binds, said peptides comprising a soluble peptide migrating in the range of 43K to 35K as determined by sodium dodecyl sulfate polyacrylamide gel electrophoresis obtained by performing said electrophoresis under reducing conditions, said peptide further comprising epitopes to which monoclonal antibodies to cytokeratin 8 bind and to which monoclonal antibodies to cytokeratins 18 or 19 bind, said peptide not binding to antibodies to vimentin.

3. The soluble peptide of claim 2, comprising epitopes to which monoclonal antibodies to cytokeratin 18 bind and to which antibodies to cytokeratin 19 bind.

4. The antigen of claim 1 comprising the partial amino acid sequence V L E V D P N I Q A V R T Q.

* * * * *

UNITED STATES PATENT AND TRADEMARK OFFICE
CERTIFICATE OF CORRECTION

PATENT NO. : 5,338,832

DATED : August 16, 1994

INVENTOR(S) : POMATO ET AL.

It is certified that error appears in the above-identified patent and that said Letters Patent is hereby corrected as shown below:

Claim 2, Column 12, line 48, delete "peptides" and insert -- peptide -- therefor.

Signed and Sealed this

Twenty-fifth Day of October, 1994

*Attest:*

*Attesting Officer*

BRUCE LEHMAN

*Commissioner of Patents and Trademarks*